United States Patent
Ueda (10) Patent No.: US 9,761,432 B2
(45) Date of Patent: Sep. 12, 2017

(54) TANDEM QUADRUPOLE MASS SPECTROMETER

(71) Applicant: SHIMADZU CORPORATION, Kyoto (JP)

(72) Inventor: Manabu Ueda, Kyotanabe (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/718,842

(22) Filed: May 21, 2015

(65) Prior Publication Data

US 2016/0343562 A1 Nov. 24, 2016

Related U.S. Application Data

(62) Division of application No. 14/442,650, filed as application No. PCT/JP2012/080327 on Nov. 22, 2012, now Pat. No. 9,269,551.

(51) Int. Cl.
*H01J 49/00* (2006.01)
*H01J 49/42* (2006.01)

(52) U.S. Cl.
CPC ........ *H01J 49/4215* (2013.01); *H01J 49/005* (2013.01)

(58) Field of Classification Search
CPC ........ H01J 49/005; H01J 49/004; H01J 49/24; H01J 49/0031
See application file for complete search history.

(56) References Cited

U.S. PATENT DOCUMENTS 5,248,875 A * 9/1993 Douglas ................ H01J 49/005
                                                                               250/281
9,419,684 B2 * 8/2016 Kuroda ................ H04B 5/0018
(Continued)

FOREIGN PATENT DOCUMENTS

CA     2 628 924 A1    5/2007
CN    102308361 A     1/2012
(Continued)

OTHER PUBLICATIONS

International Written Opinion issued Feb. 12, 2013 for PCT/JP2012/080327.
(Continued)

*Primary Examiner* — Wyatt Stoffa
(74) *Attorney, Agent, or Firm* — Sughrue Mion, PLLC (57) ABSTRACT

A dwell time calculation table (51a) showing a correspondence relation between a CID gas pressure inside a collision cell (31) and a dwell time for data collection is stored in a processing condition parameter memory (51) of a controller (50). In the table (51a), as the CID gas pressure becomes higher, the dwell time becomes longer. When an instruction to execute an MRM measurement mode is given, the controller (50) determines the dwell time in accordance with the currently set CID gas pressure, and controls a data collector (41) to accumulate detection signals from an ion detector (34) during the determined dwell time and obtain the accumulated value. If the CID gas pressure inside the collision cell (31) is high, a decrease in ion speed becomes remarkable, and the rising of the ion intensity becomes slow. However, if the dwell time becomes long, influences of the slow rising on the accumulated value are relatively reduced, and the accuracy of the accumulated value is enhanced. Accordingly, the quantitative accuracy can be enhanced.

8 Claims, 5 Drawing Sheets

(56) References Cited

U.S. PATENT DOCUMENTS

| | | | |
|---|---|---|---|
| 2003/0222210 A1* | 12/2003 | Stott | H01J 49/429 |
| | | | 250/282 |
| 2004/0026613 A1* | 2/2004 | Bateman | H01J 49/062 |
| | | | 250/281 |
| 2006/0151689 A1* | 7/2006 | Bateman | H01J 49/0031 |
| | | | 250/288 |
| 2007/0158546 A1* | 7/2007 | Lock | H01J 49/005 |
| | | | 250/282 |
| 2008/0078926 A1* | 4/2008 | Russ, IV | H01J 49/004 |
| | | | 250/282 |
| 2009/0014645 A1* | 1/2009 | Chernushevich | H01J 49/0077 |
| | | | 250/292 |
| 2009/0065690 A1* | 3/2009 | Bateman | H01J 49/0031 |
| | | | 250/282 |
| 2010/0065731 A1* | 3/2010 | Kawana | H01J 49/4215 |
| | | | 250/281 |
| 2010/0288922 A1* | 11/2010 | Itoi | H01J 49/0045 |
| | | | 250/289 |
| 2011/0215237 A1* | 9/2011 | Bateman | H01J 49/0031 |
| | | | 250/282 |
| 2011/0248160 A1* | 10/2011 | Belov | H01J 49/0031 |
| | | | 250/283 |
| 2011/0284740 A1* | 11/2011 | Okumura | H01J 49/0045 |
| | | | 250/288 |
| 2012/0091334 A1* | 4/2012 | Guna | H01J 49/26 |
| | | | 250/283 |
| 2012/0286148 A1* | 11/2012 | Kawana | H01J 49/0077 |
| | | | 250/281 |
| 2012/0326027 A1* | 12/2012 | Sugiyama | H01J 49/0009 |
| | | | 250/283 |
| 2013/0214146 A1* | 8/2013 | Okumura | H01J 49/0009 |
| | | | 250/281 |
| 2013/0299689 A1* | 11/2013 | Loboda | H01J 49/0031 |
| | | | 250/282 |
| 2014/0246576 A1* | 9/2014 | Gilbert | H01J 49/0031 |
| | | | 250/282 |
| 2015/0268203 A1* | 9/2015 | Asano | G01N 30/72 |
| | | | 250/288 |
| 2016/0126076 A1* | 5/2016 | Baba | H01J 49/063 |
| | | | 250/489 |

FOREIGN PATENT DOCUMENTS

| | | |
|---|---|---|
| DE | 203 21 731 U1 | 5/2009 |
| EP | 2 187 204 A1 | 5/2010 |
| EP | 2 395 538 | 12/2011 |
| GB | 2 435 713 | 9/2007 |
| JP | 2009-516842 A | 4/2009 |
| JP | 2009-516843 A | 4/2009 |
| JP | 2009266445 A | 11/2009 |
| WO | 2007/060437 A2 | 5/2007 |
| WO | 2009/037725 A1 | 3/2009 |
| WO | 2009/095958 A1 | 8/2009 |

OTHER PUBLICATIONS

International Search Report for PCT/JP2012/080327 dated Feb. 12, 2013.
Extended European Search Report issued Sep. 7, 2015 in European Patent Application No. 15167713.5.
Watson et al., "Introduction to Mass Spectrometry: Instrumentation, Applications, and Strategies for data Interpretation", Chapter 3, Fourth edition; 2007.
Communication dated Feb. 23, 2016, issued by the Japan Patent Office in corresponding Japanese Application No. 2015-101072.
Communication dated Jul. 22, 2016 from the European Patent Office in counterpart European application No. 12 888 969.8.
Communication dated Aug. 2, 2016, from the State Intellectual Property Office of the P.R.C., in counterpart Chinese application No. 201510337328.7.
Communication dated Aug. 8, 2016, from the State Intellectual Property Office of the P.R.C., in counterpart Chinese application No. 201280077238.3.

* cited by examiner

Fig. 3A
LOW CID GAS PRESSURE

Fig. 3B
HIGH CID GAS PRESSURE

Fig. 4A LOW CID GAS PRESSURE

Fig. 4B HIGH CID GAS PRESSURE

TANDEM QUADRUPOLE MASS SPECTROMETER

CROSS REFERENCE TO RELATED APPLICATIONS

This application is a Divisional of U.S. application Ser. No. 14/442,650, filed May 13, 2015, which is a National Stage of International Application No. PCT/JP2012/080327 filed Nov. 22, 2012, the contents of all of which are incorporated herein by reference in their entirety.

TECHNICAL FIELD

The present invention relates to a tandem quadrupole mass spectrometer which dissociates ions having a specific mass-to-charge ratio m/z through collision-induced dissociation (CID) or the like and performs a mass spectrometric analysis on product ions (fragment ions) produced through the dissociation.

BACKGROUND ART

A method called an MS/MS analysis (also called a tandem analysis) is known as one of the mass spectrometric analysis techniques for identification and structural analyses of substances having large molecular weights. A tandem quadrupole mass spectrometer (also called a triple quadrupole mass spectrometer) having a relatively simple and inexpensive structure is one of the widely used mass spectrometers capable of performing the MS/MS analysis.

As disclosed in Patent Literature 1, generally in the tandem quadrupole mass spectrometer, quadrupole mass filters are provided respectively before and after (i.e. at the front stage and rear stage of) a collision cell for dissociating ions, where precursor ions are selected by the front-stage quadrupole mass filter from among a variety of ions originating from a target compound, and product ions are separated by the rear-stage quadrupole mass filter in accordance with their mass-to-charge-ratios. The collision cell has a box-like, relatively tight-sealed structure, and a CID gas such as argon and nitrogen is introduced into the collision cell. The precursor ions selected by the front-stage quadrupole mass filter are introduced into the collision cell endowed with appropriate collision energy, and collide with the CID gas inside the collision cell. As a result, collision-induced dissociation occurs, and the product ions are produced.

The dissociation efficiency of ions inside the collision cell depends on the amount of collision energy of the ions, the CID gas pressure inside the collision cell, and the like. Hence, the detection sensitivity of the product ions that have passed through the rear-stage quadrupole mass filter also depends on the amount of collision energy and the CID gas pressure.

In the tandem quadrupole mass spectrometer, a measurement in a multiple reaction monitoring (MRM) mode is performed in many cases, in order to perform quantitative determination on a known compound with high accuracy and sensitivity. In the MRM measurement mode, for both the front-stage and rear-stage quadrupole mass filters, the mass-to-charge-ratios of the ions that pass through the filters are fixed. Hence, in conventional tandem quadrupole mass spectrometers, the CID gas pressure inside the collision cell is set to a value (normally, at several mTorr) that is determined in advance by a manufacturer such that the detection sensitivity is as high as possible in the MRM measurement mode. Of course, the CID gas supply pressure can be manually adjusted by a user, whereby a measurement can be performed with higher sensitivity than that under such a preset condition as described above, with regard to, for example, a specific compound.

In general, as the CID gas pressure inside the collision cell becomes higher, ions become more likely to contact the CID gas, and hence the dissociation efficiency of the ions becomes higher. However, the kinetic energy of the ions is attenuated by the collision with the CID gas, and hence the flight speed of the ions as a whole decreases. In the case of the MRM measurement mode, dissociation of precursor ions having a given mass-to-charge-ratio and selection and detection of product ions having a given mass-to-charge-ratio are performed for a certain amount of time, and hence the decrease in ion flight speed in the collision cell as described above is considered to have relatively small influences on the ion intensity. However, in actuality, even in the MRM measurement mode, if the CID gas pressure is raised, the ion intensity obviously decreases compared with the case where the CID gas pressure is low. As a result, there arises a problem that a sufficiently high peak cannot be obtained on a mass chromatogram at a mass-to-charge-ratio corresponding to a target compound and that the quantitative accuracy thus decreases.

Moreover, a wide variety of measurement modes other than the MRM measurement mode described above are prepared for the tandem quadrupole mass spectrometer. Examples of the other measurement modes include: measurement modes in which both the front-stage and rear-stage quadrupole mass filters perform ion selection (a precursor ion scan measurement mode, a product ion scan measurement mode, a neutral loss scan measurement mode, and the like); and measurement modes in which one of the front-stage and rear-stage quadrupole mass filters does not perform ion selection (namely, all ions pass through the filter intact) while the other of the front-stage and rear-stage quadrupole mass filters performs a mass scan. In general, in all measurement modes except for measurement modes in which CID is not performed inside the collision cell, the CID gas pressure inside the collision cell is set to a value that is determined in advance by the manufacturer such that the detection sensitivity is as high as possible in the MRM measurement mode, as described above.

However, under such control, in the precursor ion scan measurement mode and the neutral loss scan measurement mode in which the front-stage quadrupole mass filter performs a scan over a predetermined mass-to-charge-ratio range, a mass-to-charge-ratio deviation of a target ion peak on a mass spectrum (MS/MS spectrum), which results from the decrease in ion flight speed inside the collision cell as described above, tends to become large. The degree of the decrease in ion flight speed inside the collision cell also depends on the ion size (which normally corresponds to the mass-to-charge-ratio). Hence, the degree of the mass-to-charge-ratio deviation on the mass spectrum is not always constant, and it is not easy to obtain the amount of deviation and correct the deviation. Moreover, variation in flight speed increases even among ions having the same mass-to-charge-ratio, and this causes a problem that the peak width becomes large on the mass spectrum, resulting in a decrease in mass resolution.

Furthermore, the MRM measurement mode is used in many cases for a simultaneous multicomponent analysis by a liquid chromatograph mass spectrometer or a gas chromatograph mass spectrometer, and the number of pairs of a precursor ion and a product ion to be detected simultaneously in parallel increases if the number of measurement target compounds increases. To deal with this, it is necessary to make high-speed switching of the mass-to-charge-ratio of ions that are allowed to pass through the front-stage quadrupole mass filter. As a result, such influences of the decrease in ion intensity as described above become further remarkable. On the other hand, even though the number of measurement target compounds is decreased in order to perform a measurement on each compound with high sensitivity, the improvement in sensitivity is limited.

CITATION LIST

Patent Literature

[Patent Literature 1] WO 2009/095958 A

SUMMARY OF INVENTION

Technical Problem

The present invention, which has been made in order to solve the above-mentioned problems, has a first object to provide a tandem quadrupole mass spectrometer capable of minimizing a decrease in sensitivity caused by raising a CID gas pressure inside a collision cell in an MRM measurement or the like.

The present invention further has a second object to provide a tandem quadrupole mass spectrometer capable of reducing a mass-to-charge-ratio deviation on a mass spectrum obtained in a precursor ion scan measurement, a neutral loss scan measurement, or the like.

The present invention further has a third object to provide a tandem quadrupole mass spectrometer capable of performing an appropriate measurement suited to intended measurement conditions and intended measurement purpose in the case, for example, where a high-speed measurement is necessary because the number of measurement target compounds is large in a simultaneous multicomponent analysis or where a high-sensitivity measurement is desired to be performed because the number of measurement target compounds is relatively small.

Solution to Problem

A first specific form of the present invention, which has been made in order to achieve the above-mentioned first object, provides a tandem quadrupole mass spectrometer including: a front-stage quadrupole mass filter for selecting, as precursor ions, ions having a specific mass-to-charge-ratio from among a variety of ions; a collision cell for causing the precursor ions to collide with a predetermined gas to dissociate the ions; a rear-stage quadrupole mass filter for selecting ions having a specific mass-to-charge-ratio from among a variety of product ions produced through the dissociation; and a detector for detecting the selected product ions, the tandem quadrupole mass spectrometer further including:

a) a gas adjuster for adjusting a supply pressure or a supply flow rate of a gas supplied to an inside of the collision cell such that a gas pressure inside the collision cell is in a desired state; and b) a controller for changing a length of a dwell time in accordance with the gas supply pressure or the gas supply flow rate set by the gas adjuster or a target gas pressure when a measurement in a multiple reaction monitoring measurement mode is performed, the dwell time being a period of time to take in signals obtained by the detector with regard to precursor ions and product ions originating from one compound.

A second specific form of the present invention, which has been made in order to achieve the above-mentioned first object, provides a tandem quadrupole mass spectrometer including: a front-stage quadrupole mass filter for selecting, as precursor ions, ions having a specific mass-to-charge-ratio from among a variety of ions; a collision cell for causing the precursor ions to collide with a predetermined gas to dissociate the ions; a rear-stage quadrupole mass filter for selecting ions having a specific mass-to-charge-ratio from among a variety of product ions produced through the dissociation; and a detector for detecting the selected product ions, the tandem quadrupole mass spectrometer further including:

a) a gas adjuster for adjusting a supply pressure or a supply flow rate of a gas supplied to an inside of the collision cell such that a gas pressure inside the collision cell is in a desired state; and b) a controller for changing a length of a settling time in accordance with the gas supply pressure or the gas supply flow rate set by the gas adjuster or a target gas pressure when a measurement in a multiple reaction monitoring (MRM) measurement mode is performed, the settling time being an allowance time necessary for settling of a voltage applied to the front-stage and/or rear-stage quadrupole mass filter when the applied voltage is changed in order to perform a measurement with at least one of precursor ions and product ions being different, after signals obtained by the detector with regard to precursor ions and product ions originating from one compound are taken in.

In the tandem quadrupole mass spectrometer according to each of the first and second specific forms, examples of the detector include a detector including a multi-stage dynode secondary electron multiplier and a detector including a conversion dynode, a fluorescent material, and a photoelectron multiplier in combination. Detection signals obtained by the detector thus configured are accumulated or averaged during the dwell time, whereby measurement data on a given point is obtained. Moreover, in the case where ions originating from a plurality of compounds need to be measured simultaneously in parallel in the MRM measurement mode, the voltage applied to the front-stage and/or rear-stage quadrupole mass filter is changed at the time of switching of measurement target ions, and hence the settling time is set such that data acquisition is suspended until the applied voltage settles.

In the first specific form, the controller changes the dwell time in accordance with the gas supply pressure or the gas supply flow rate set by the gas adjuster or the target gas pressure. In the second specific form, the controller changes not the dwell time but the settling time in accordance with the gas supply pressure or the gas supply flow rate set by the gas adjuster or the target gas pressure. More specifically, the controller lengthens the dwell time or the settling time in the case where the gas supply pressure, the gas supply flow rate, or the target gas pressure is high or large, namely, in the case where ions are more likely to contact the gas inside the collision cell, compared with the case where the gas supply pressure, the gas supply flow rate, or the target gas pressure is not high or large. In the case where ions are more likely to contact the gas inside the collision cell, the degree of a decrease in ion flight speed becomes high, and the time delay until ions reach the detector becomes larger. As a result, if the lengths of both the settling time and the dwell time are not changed, data acquisition is unfavorably restarted before the ion intensity sufficiently rises after the voltage applied to the front-stage and/or rear-stage quadrupole mass filter is changed. If the insufficiently rising ion intensity as described above is included in the accumulated value, the accuracy and the sensitivity of the accumulated value become relatively low. This tendency becomes more remarkable as the CID gas pressure inside the collision cell becomes higher.

In the tandem quadrupole mass spectrometer according to the first specific form, the dwell time is lengthened in the case where the gas pressure inside the collision cell is high and where the rising of the ion intensity is slow. Hence, even if the rising of the ion intensity is insufficient as described above, the ion intensity has smaller influences on the accumulated value, and the accuracy and the sensitivity of the accumulated value are enhanced. Moreover, in the tandem quadrupole mass spectrometer according to the second specific form, in the case where the gas pressure inside the collision cell is high and where the rising of the ion intensity is slow, the settling time is lengthened, namely, the start timing of data collection is delayed. Hence, even if the rising of the ion intensity is insufficient, the ion intensity has smaller influences on the accumulated value, and the accuracy and the sensitivity of the accumulated value are enhanced. In any case, the accuracy and the sensitivity of the signal intensity for each compound in the MRM measurement mode are enhanced, and the accuracy of an area value of a peak on a mass chromatogram is enhanced, whereby the quantitative accuracy is increased.

A third specific form of the present invention, which has been made in order to achieve the above-mentioned second object, provides a tandem quadrupole mass spectrometer including: a front-stage quadrupole mass filter for selecting, as precursor ions, ions having a specific mass-to-charge-ratio from among a variety of ions; a collision cell for causing the precursor ions to collide with a predetermined gas to dissociate the ions; a rear-stage quadrupole mass filter for selecting ions having a specific mass-to-charge-ratio from among a variety of product ions produced through the dissociation; and a detector for detecting the selected product ions, the tandem quadrupole mass spectrometer further including:

a) a mode setter for enabling a user to set a measurement mode to be executed;

b) a gas supplier for supplying the predetermined gas to an inside of the collision cell; and c) a controller for controlling the gas supplier such that a CID gas pressure inside the collision cell is changed in accordance with the measurement mode set by the mode setter.

In the tandem quadrupole mass spectrometer according to the third specific form, the controller controls the gas supplier to switch the CID gas pressure inside the collision cell in accordance with the kind of measurement mode to be executed. Specifically, in the case where a decrease in ion speed inside the collision cell becomes significant, the CID gas pressure is lowered such that influences of the decrease in ion speed relatively lower.

For example, the controller may lower the CID gas pressure inside the collision cell in a case where the set measurement mode is a measurement mode in which the front-stage quadrupole mass filter performs a mass scan and ions are dissociated inside the collision cell, compared with a case where the set measurement mode is a measurement mode in which the front-stage quadrupole mass filter does not perform a mass scan. Here, the measurement mode in which the front-stage quadrupole mass filter performs the mass scan and the ions are dissociated inside the collision cell includes: a precursor ion scan measurement mode; a neutral loss scan measurement mode; and a measurement mode in which only the front-stage quadrupole mass filter performs the mass scan while the rear-stage quadrupole mass filter does not perform ion selection according to a mass-to-charge-ratio.

In the above-mentioned measurement modes, the mass-to-charge-ratio of precursor ions introduced into the collision cell changes so as to increase or decrease with the lapse of time, and hence the ion passage time inside the collision cell becomes long. In particular, if a difference in ion passage time becomes large depending on a mass-to-charge-ratio, a decrease in mass accuracy of a mass spectrum becomes remarkable. In view of this, in the tandem quadrupole mass spectrometer according to the third specific form, when these measurement modes are executed, the CID gas pressure inside the collision cell becomes relatively low, and the ion passage time inside the collision cell becomes short. Hence, a mass-to-charge-ratio deviation can be reduced, and the mass accuracy of a mass spectrum can be secured.

Moreover, in order to achieve the above-mentioned third object, in the tandem quadrupole mass spectrometer according to the third specific form, at least a high-speed mode in which greater importance is placed on a measurement speed than on a detection sensitivity and a high-sensitivity mode in which greater importance is placed on the detection sensitivity than on the measurement speed may be prepared for a multiple reaction monitoring (MRM) measurement mode, as measurement modes selectable by the mode setter, and the controller may lower the CID gas pressure inside the collision cell in a case where the set measurement mode is the high-speed mode of the MRM measurement mode, compared with a case where the set measurement mode is the high-sensitivity mode of the MRM measurement mode.

Here, the high-speed mode is a mode that is used in an MRM measurement in the case where the number of mass-to-charge-ratio pairs of a precursor ion and a product ion to be measured simultaneously in parallel is large, specifically, in the case where the number of measurement target compounds is specially large in a simultaneous multicomponent analysis or where the linear speed of a mobile phase in a liquid chromatograph or a gas chromatogram connected in the front stage of the mass spectrometer is high. On the other hand, the high-sensitivity mode is a mode that is used in the case where the number of kinds of compounds contained in a sample is small and where high-accuracy quantitative determination is desired to be performed on each compound.

In the case where the high-speed mode is set, the CID gas pressure inside the collision cell is relatively lowered. Hence, the ion passage time inside the collision cell can be suppressed to be short, and, for example, the following problem can be avoided. That is, when a product ion produced by dissociating a given precursor ion tries to pass through the rear-stage quadrupole mass filter, the mass-to-charge-ratio of ions that are allowed to pass through this mass filter is unfavorably changed to the mass-to-charge-ratio of product ions that are not paired with the given precursor ion. Consequently, even in the case where the time allotted to each mass-to-charge-ratio pair (each channel to be described later) of a precursor ion and a product ion is short, a product ion produced from a target precursor ion can be reliably detected. In this case, however, the ion dissociation efficiency inside the collision cell is relatively low, and hence an improvement in detection sensitivity itself is difficult.

In the case where the high-sensitivity mode is set, the CID gas pressure inside the collision cell is relatively raised, and hence the ion dissociation efficiency inside the collision cell becomes high. In this case, although the ion passage time inside the collision cell is long, a high-speed measurement is not required, and hence the voltage applied to the rear-stage quadrupole mass filter can be maintained until delayed product ions completely finish passing through this mass filter. Consequently, a sufficient number of ions can reach the detector, and high detection sensitivity can be achieved.

In this way, measurements respectively suitable for both the case where greater importance is placed on high speed and the case where greater importance is placed on high detection sensitivity can be performed in the MRM measurement mode.

Advantageous Effects of Invention

In the tandem quadrupole mass spectrometer according to each of the first and second specific forms of the present invention, even in the case where the CID gas pressure inside the collision cell is raised in the MRM measurement, a decrease in detection sensitivity can be minimized, and the accuracy of an area value of a peak originating from a target compound on a mass chromatogram can be enhanced, whereby high quantitative accuracy can be achieved.

Moreover, in the tandem quadrupole mass spectrometer according to the third specific form of the present invention, if the CID gas pressure is changed in accordance with measurement modes such as the precursor ion scan measurement mode and the neutral loss scan measurement mode, a mass-to-charge-ratio deviation on a mass spectrum created in each of these scan measurement modes can be reduced. Furthermore, in the tandem quadrupole mass spectrometer according to the third specific form of the present invention, if the CID gas pressure is changed in accordance with measurement modes such as the high-speed mode and the high-sensitivity mode of the MRM measurement, measurements respectively suitable for both the case where greater importance is placed on high speed and the case where greater importance is placed on high detection sensitivity can be performed.

DESCRIPTION OF EMBODIMENTS

Hereinafter, a first embodiment of a liquid chromatograph tandem quadrupole mass spectrometer (hereinafter, called a "LC/MS/MS") including a tandem quadrupole mass spectrometer according to the present invention is described with reference to the attached drawings.

Figure 1:
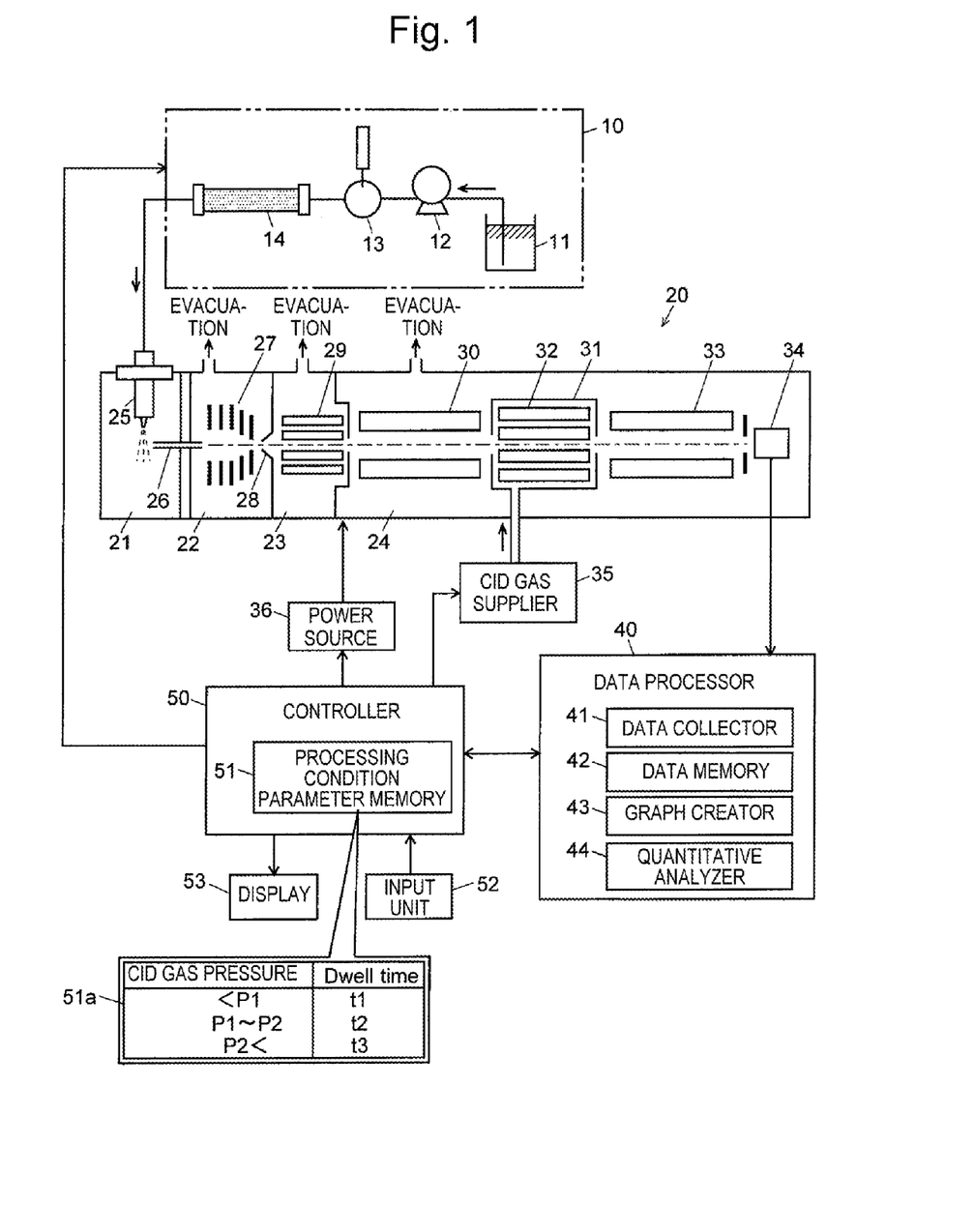
FIG. 1 is a schematic configuration diagram of a main part of a first embodiment of an LC/MS/MS including a tandem quadrupole mass spectrometer according to the present invention.

In the LC/MS/MS of the first embodiment, a liquid chromatograph unit 10 includes: a mobile phase container 11 for holding a mobile phase; a pump 12 for drawing and supplying the mobile phase at a constant flow rate; an injector 13 for injecting a predetermined amount of prepared sample into the mobile phase; and a column 14 for temporally separating a variety of compounds contained in the sample. The pump 12 draws the mobile phase from the mobile phase container 11 and supplies the drawn mobile phase into the column 14 at a constant flow rate. When a predetermined amount of sample liquid is introduced from the injector 13 into the mobile phase, the sample is carried by the mobile phase and introduced into the column 14. While passing through the column 14, the variety of compounds in the sample are temporally separated, to be eventually eluted from the outlet of the column 14 and introduced into a mass spectrometer 20.

The mass spectrometer 20 has the configuration of a multi-stage differential pumping system including an ionization chamber 21 maintained at approximately atmospheric pressure and a high-vacuum analysis chamber 24 evacuated by a high-performance vacuum pump (not shown), between which first and second intermediate vacuum chambers 22 and 23 each having a degree of vacuum increased in a stepwise manner are provided. The ionization chamber 21 has an electrospray ionization probe 25 for spraying sample solution while electrically charging this solution. The ionization chamber 21 communicates with the first intermediate vacuum chamber 22 in the next stage through a thin heated capillary 26. The first and second intermediate vacuum chambers 22 and 23 are separated by a skimmer 28 having a small hole at its apex. Ion guides 27 and 29 for transporting ions to the subsequent stage while converging the ions are provided in the first and second intermediate vacuum chambers 22 and 23, respectively. The analysis chamber 24 contains a collision cell 31 including a multi-pole ion guide 32, a front-stage quadrupole mass filter 30 for separating ions according to their mass-to-charge ratios and a rear-stage quadrupole mass filter 33 for similarly separating ions according to their mass-to-charge ratios being provided before and after the collision cell 31. An ion detector 34 is also provided in the analysis chamber 24. A CID gas supplier 35 supplies a CID gas such as argon or nitrogen into the collision cell 31. A power source 36 applies predetermined voltages to the electrospray ionization probe 25, the ion guides 27, 29, and 32, the quadrupole mass filters 30 and 33, and other components, respectively.

In the mass spectrometer 20, when the eluate from the column 14 reaches the electrospray ionization probe 25, the eluate is sprayed while being supplied with electric charges from the tip of the probe 25. The electrically charged droplets thus formed by the spraying process are progressively broken into smaller sizes by an electrostatic force due to the supplied electric charges. During this process, the solvent is vaporized, and ions originating from the compounds are ejected. The ions thus produced are sent through the heated capillary 26 into the first intermediate vacuum chamber 22, where the ions are converged by the ion guide 27 and sent through the small hole at the apex of the skimmer 28 into the second intermediate vacuum chamber 23. In this chamber, the ions originating from the compounds are converged by the ion guide 29 and sent into the analysis chamber 24, where the ions are introduced into the space extending along the longitudinal axis of the front-stage quadrupole mass filter 30. It should be naturally understood that the ionization method is not limited to the electrospray ionization but other methods may be used, such as atmospheric pressure chemical ionization or atmospheric pressure photoionization.

When an MS/MS analysis is performed in the mass spectrometer 20, a predetermined voltage (composed of a high-frequency voltage and a DC voltage superposed on each other) is applied from the power source 36 to each of the rod electrodes of the front-stage quadrupole mass filter 30 and the rear-stage quadrupole mass filter 33, while the CID gas is continuously or intermittently supplied from the CID gas supplier 35 into the collision cell 31. Among the variety of ions sent into the front-stage quadrupole mass filter 30, only ions having a specific mass-to-charge ratio corresponding to the voltage applied to each rod electrode of the front-stage quadrupole mass filter 30 are allowed to pass through this filter 30 and be introduced into the collision cell 31 as precursor ions. In the collision cell 31, the precursor ions collide with the CID gas and are thus dissociated, so that a variety of product ions are produced. The variety of produced product ions are introduced into the rear-stage quadrupole mass filter 33, where only product ions having a specific mass-to-charge ratio corresponding to the voltage applied to each rod electrode of the rear-stage quadrupole mass filter 33 are allowed to pass through this filter 33, to eventually reach and be detected by the ion detector 34. The ion detector 34 is a pulse-counting detector, and outputs pulse signals whose number corresponds to the number of incident ions, as detection signals.

A data processor 40 includes functional blocks such as a data collector 41, a data memory 42, a graph creator 43, and a quantitative analyzer 44. A controller 50 to which an input unit 52 and a display 53 are connected controls the operations of the pump 12 and the injector 13 in the liquid chromatograph unit 10 as well as those of the power source 36 and the CID gas supplier 35 in the mass spectrometer 20. At least part of the functions of the controller 50 and the data processor 40 can be realized by installing a dedicated controlling and processing software program on a personal computer provided as hardware resources and executing this program on the computer.

When a quantitative analysis is performed by the LC/MS/MS configured as described above, an MRM measurement mode in which each of the front-stage quadrupole mass filter 30 and the rear-stage quadrupole mass filter 33 allows only ions having a predetermined mass-to-charge-ratio to pass through the filter is used in many cases. Accordingly, description is given below of the case where a specific product ion corresponding to a specific precursor ion originating from a target compound is detected in the MRM measurement mode. In general, the MRM measurement can be performed with a plurality of channels being set, and a mass-to-charge-ratio pair of a precursor ion and a product ion is defined for each of the channels.

Figure 2:
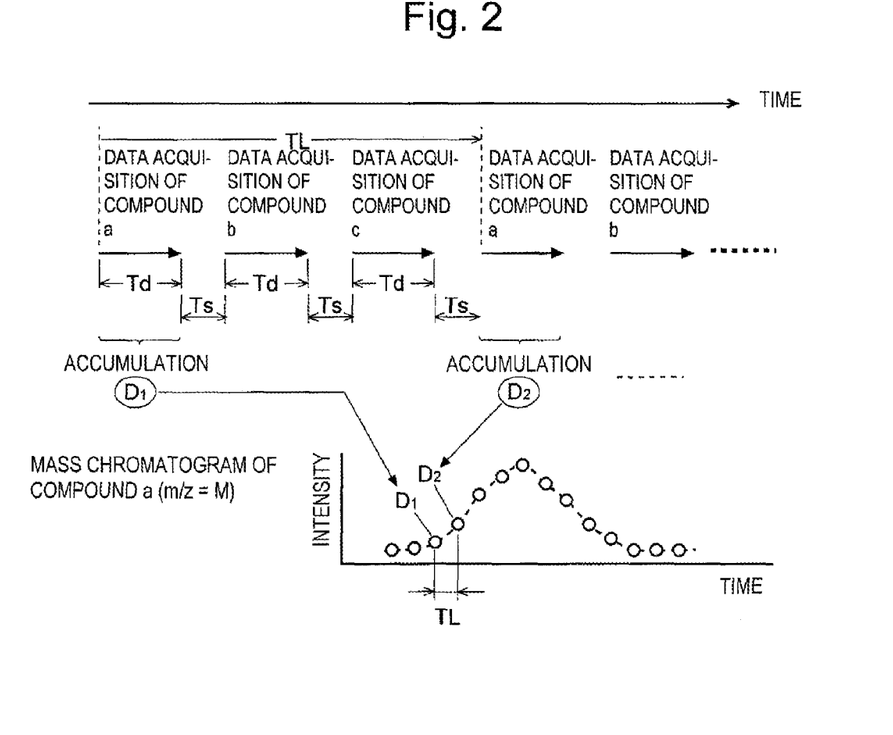
FIG. 2 is a diagram for describing acquisition timing of data in an MRM measurement mode and a mass chromatogram based on the data.

FIG. 2 is a diagram for describing acquisition timing of data and a mass chromatogram based on the data in the case where the MRM measurement of three channels is performed. For each channel, in order to perform quantitative determination on a given compound, the signal intensity is measured for precursor ions and product ions each having a mass-to-charge-ratio characteristic of the given compound. As shown in FIG. 2, the measurement is performed once for each of the plurality of channels in one measurement cycle having a time length of a loop time TL. Moreover, the product ions originating from each compound are detected during a dwell time Td. A break time Ts between the dwell time Td for one compound (for example, a compound a) and the dwell time Td for another compound (for example, a compound b) is a settling time set as an allowance time necessary for settling of the voltage applied to each of the quadrupole mass filters 30 and 33 when the applied voltage is changed in order to change the mass-to-charge-ratio of ions that are allowed to pass through each filter.

The data collector 41 in the data processor 40 has a function of counting pulse signals sent from the ion detector 34. As described above, during a period of the settling time Ts, the mass-to-charge-ratios of ions that pass through the quadrupole mass filters 30 and 33 are not secured. Hence, the data collector 41 discards pulse signals inputted during the settling time Ts without counting the same, accumulates the number of pulse signals inputted during the dwell time Td, and converts the accumulation result into digital data indicating the number of ions that reach the ion detector 34. Accordingly, as shown in FIG. 2, data corresponding to, for example, the compound a is obtained as $D_1, D_2, \ldots$ for each loop time TL. Pieces of data corresponding to the other compounds b and c are similarly obtained, and the obtained pieces of data are stored into the data memory 42.

The graph creator 43 creates, for example, a mass chromatogram at a specific mass-to-charge-ratio, based on the data stored in the data memory 42, and displays the mass chromatogram on the screen of the display 53 through, for example, the controller 50. Basically, as shown in FIG. 2, the graph creator 43 can create the mass chromatogram by plotting the pieces of data $D_1, D_2, \ldots$ that are sequentially obtained at intervals of the loop time TL. The quantitative analyzer 44 detects a peak near the retention time of a target compound on the mass chromatogram, and calculates the area of the peak. Then, with reference to a standard curve that is created in advance based on measurement results of a sample containing compounds each having a known concentration, the quantitative analyzer 44 obtains a concentration (quantitative value) corresponding to the peak area value, and displays the concentration on the screen of the display 53.

As is apparent from FIG. 2, if the number of channels is the same, as the dwell time Td becomes shorter, the loop time TL becomes shorter. As the loop time TL becomes shorter, the number of measurement points for the same channel becomes larger in a given unit time, and the number of measurement points per peak on a mass chromatogram becomes larger, so that measurement reproducibility is enhanced. That is, if the dwell time Td is short, even if the time for which a given compound is introduced into the mass spectrometer 20 is short, namely, even if the linear speed of the mobile phase in the liquid chromatograph unit 10 is high, the accuracy of a peak area value on a mass chromatogram can be enhanced, and high quantitative accuracy can be secured.

Figure 5:
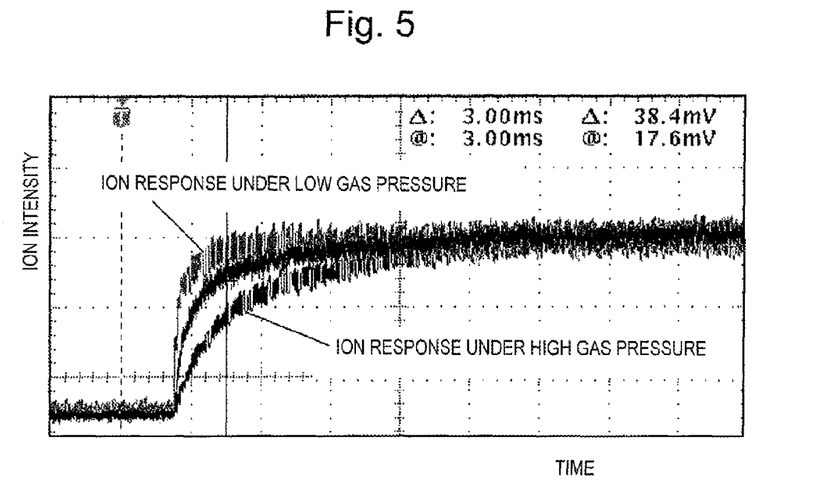
FIG. 5 is a waveform diagram showing actual measurement results of an ion signal response time under conditions of different CID gas pressures.

However, if the dwell time Td is short, the following problem occurs. FIG. 5 is a diagram showing actual measurement results of an ion intensity response time of ions originating from reserpine in the case where the supply pressure of the CID gas supplied to the collision cell 31 is changed in two (high and low) stages. Under the high gas pressure, the rising of the ion intensity is slower than under the low gas pressure, and the response time until the ion intensity becomes substantially constant is significantly long. This is for the following reason: if the CID gas pressure inside the collision cell 31 is high, a decrease in ion speed due to contact with the CID gas becomes remarkable, and the time delay until ions finally reach the ion detector 34 thus becomes larger.

Figure 6:
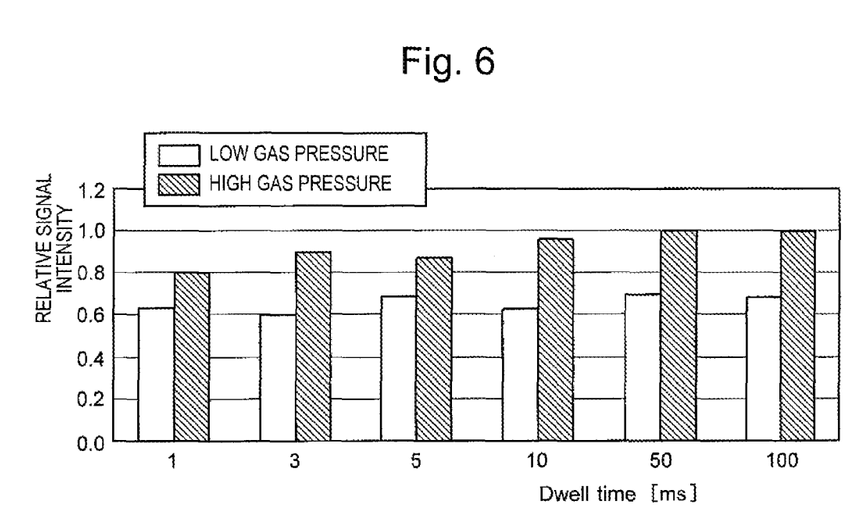
FIG. 6 is a diagram showing actual measurement results of a relation between a dwell time and a signal intensity value (accumulated value) under conditions of different CID gas pressures.

FIG. 6 is a diagram showing actual measurement results of a relation between the dwell time and the signal intensity accumulated value of reserpine ions in the case where the CID gas pressure is changed in two (high and low) stages. Under the high gas pressure, the CID efficiency is higher and the number of produced product ions is larger than under the low gas pressure. Hence, the signal intensity itself as a whole is higher. However, as the dwell time becomes shorter, a decrease in signal intensity becomes more remarkable. This is for the following reason: in the case where the CID gas pressure is high, the ion intensity response time is long as shown in FIG. 5, and hence, if the dwell time is set to be short, the slow rising of the ion intensity has relatively large influences. In comparison, in the case where the CID gas pressure is low, the ion intensity response time is short, and hence, even if the dwell time is set to be short, a decrease in signal intensity accumulated value is small.

In view of the above, in the LC/MS/MS of the present embodiment, the dwell time during which the data collector 41 accumulates pulse signals is changed in accordance with the CID gas pressure inside the collision cell 31 (actually, the supply pressure or the supply flow rate of the CID gas supplied into the collision cell 31). Specifically, in the case where the CID gas pressure is low, the dwell time is set to be shorter than in the case where the CID gas pressure is high. In order to perform such control, an appropriate dwell time value may be empirically obtained in advance by, for example, a mass spectrometer manufacturer for each of the CID gas pressures in the plurality of stages, and may be stored as a dwell time calculation table 51a shown in FIG. 1 into a processing condition parameter memory 51. In the example shown in FIG. 1, the CID gas pressure is divided into three stages of less than P1, P1 or more and less than P2, and P2 or more, and appropriate dwell time values t1, t2, and t3 are respectively associated with the three stages. The number of divisions of the CID gas pressure may be arbitrarily determined, and the dwell time may be calculated in not a table form but another form such as a calculation expression.

In the LC/MS/MS of the present embodiment, if an operator gives an instruction to execute the MRM measurement mode from the input unit 52 and inputs and sets a variety of parameters (for example, the mass-to-charge-ratios of precursor ions and product ions at each channel) necessary for this measurement mode, the controller 50 obtains the dwell time Td corresponding to the current CID gas pressure in the executed MRM measurement mode, based on the dwell time calculation table 51a stored in the processing condition parameter memory 51. Then, for each channel, the controller 50 controls the data collector 41 to accumulate pulse signals from the ion detector 34 during the obtained dwell time Td and convert the accumulation result into data.

Figure 3A:
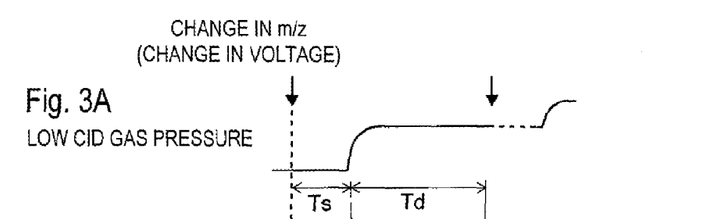
FIG. 3A and FIG. 3B are schematic waveform diagrams for describing an example characteristic data collecting operation by the LC/MS/MS in the first embodiment.
Figure 3B:
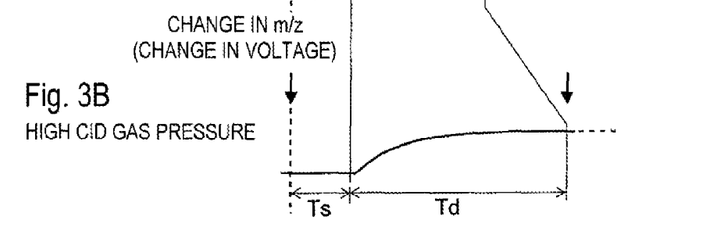

FIG. 3A and FIG. 3B are schematic waveform diagrams for describing an example data collecting operation in the case where the dwell time Td is changed as described above. As shown in FIG. 3B, under the high CID gas pressure, the rising of the ion intensity is slower and the dwell time Td is longer than under the low CID gas pressure. Hence, the counting time in the state where the ion intensity is sufficiently risen and stable is long, and the influences of the slow rising are relatively reduced. As a result, even under the high CID gas pressure, the accuracy and sensitivity of each piece of signal intensity data is enhanced. In this case, however, if the number of channels is large, the loop time is long, and hence it is desirable to: reduce the linear speed of the mobile phase in the liquid chromatograph unit 10 and thus lengthen the period during which one compound is introduced into the mass spectrometer 20; or reduce the number of channels, namely, reduce the number of compounds measured simultaneously in parallel.

As shown in FIG. 3A, in the case where the CID gas pressure is low and where the rising of the ion intensity is rapid, the dwell time Td is short. Hence, if the number of channels is the same, the loop time can be shortened. Consequently, the measurement can be finished in a short time by increasing the linear speed of the mobile phase in the liquid chromatograph unit 10. Otherwise, a large number of compounds can be measured simultaneously in parallel by increasing the number of channels.

Figure 4A:
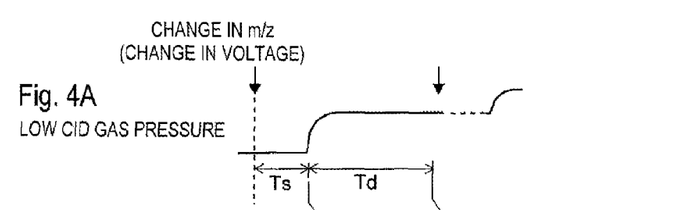
FIG. 4A and FIG. 4B are schematic waveform diagrams for describing another example characteristic data collecting operation by the LC/MS/MS in the present embodiment.
Figure 4B:
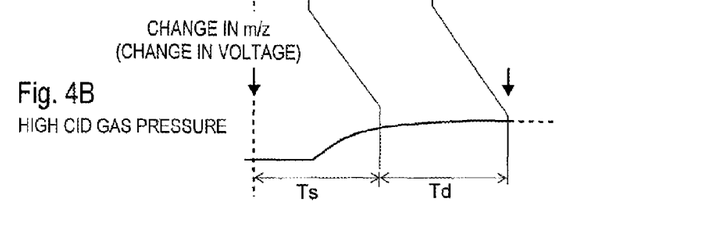

In the above description, the dwell time Td is changed in accordance with the CID gas pressure (actually, the supply pressure or the supply flow rate) inside the collision cell 31. Instead of changing the dwell time Td, the settling time Ts may be changed. FIG. 4A and FIG. 4B are schematic waveform diagrams for describing an example data collecting operation in the case where the settling time Ts is changed. As shown in FIG. 4B, if the settling time Ts is lengthened, part of a portion in which the ion intensity slowly rises, which is included in part of the dwell time Td in the case where the settling time Ts is short, is included in the settling time Ts, and is excluded from the dwell time Td. As a result, even if the length itself of the dwell time Td is constant, the proportion of the counting time in the state where the ion intensity is sufficiently risen and stable is increased, and the influences of the slow rising are relatively reduced. As a result, even under the high CID gas pressure, the accuracy and sensitivity of each piece of signal intensity data is enhanced.

Figure 7:
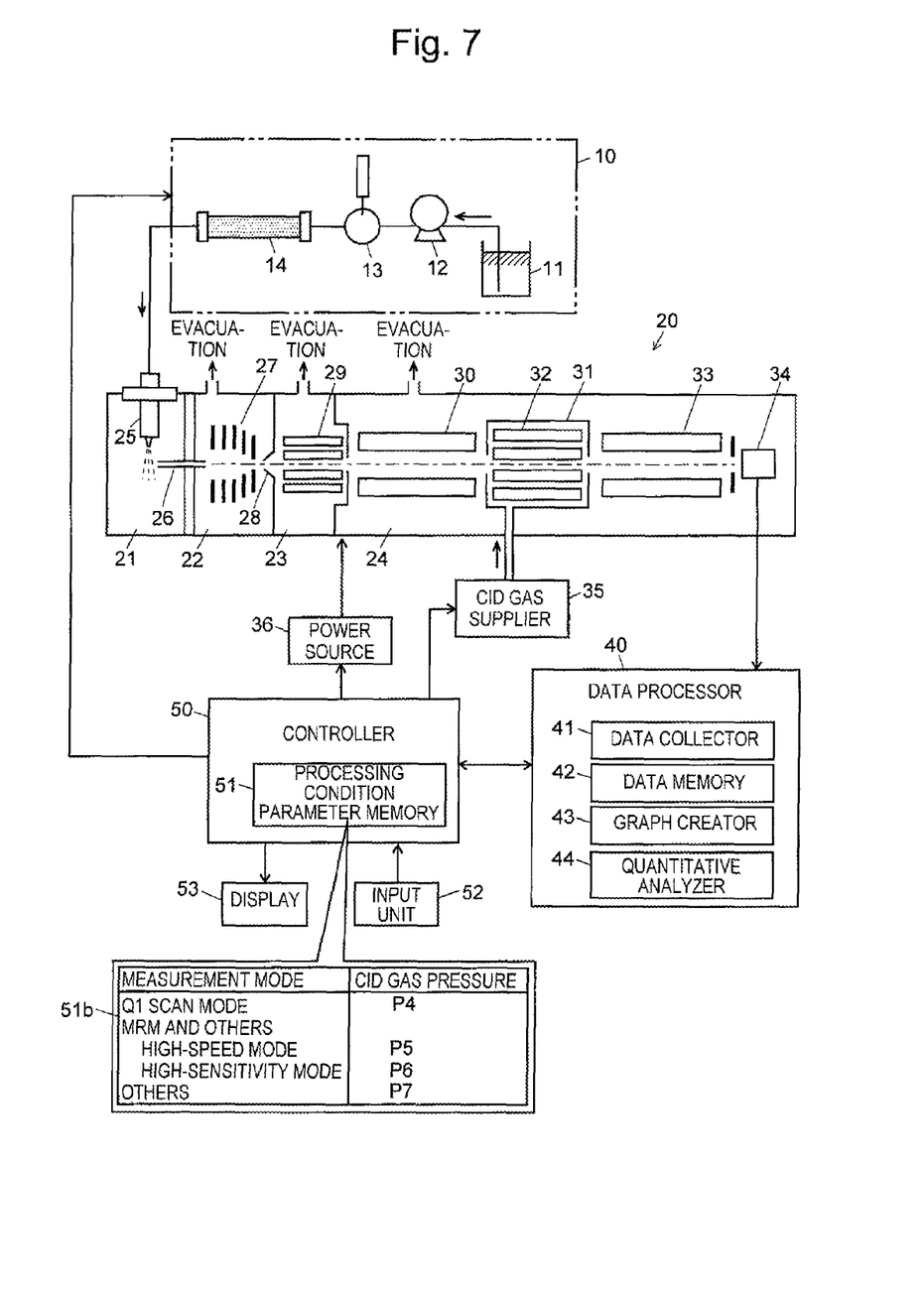
FIG. 7 is a schematic configuration diagram of a main part of a second embodiment of an LC/MS/MS including a tandem quadrupole mass spectrometer according to the present invention.

Next, a second embodiment of the LC/MS/MS including the tandem quadrupole mass spectrometer according to the present invention is described with reference to the attached drawings. FIG. 7 is a configuration diagram of a main part of the LC/MS/MS of the second embodiment, in which components that are the same as or equivalent to those in the configuration diagram of the main part of the LC/MS/MS of the first embodiment shown in FIG. 1 are denoted by the same reference signs, and detailed description thereof is omitted. In the LC/MS/MS of the second embodiment, the processing condition parameter memory 51 of the controller 50 stores an optimum CID gas pressure calculation table 51b showing a correspondence relation between a measurement mode and a CID gas pressure.

A "Q1 scan mode" in the optimum CID gas pressure calculation table 51b is a measurement mode in which, in the LC/MS/MS, the front-stage quadrupole mass filter 30 performs a mass scan and ions are dissociated through CID inside the collision cell 31. Specifically, the "Q1 scan mode" includes a precursor ion scan measurement mode, a neutral loss scan measurement mode, and a measurement mode in which: precursor ions that are selected through the mass scan by the front-stage quadrupole mass filter 30 are dissociated inside the collision cell 31; and the produced product ions are detected by the ion detector 34 without being mass-separated. The "MRM measurement mode" includes two types of a high-speed mode and a high-sensitivity mode. "Others" include measurement modes other than the above-mentioned measurement modes, for example, a product ion scan measurement mode and a measurement mode in which: all ions that pass through the front-stage quadrupole mass filter 30 intact are dissociated inside the collision cell 31; specific ions among the produced product ions are selected by the rear-stage quadrupole mass filter 33; and the selected ions are detected by the ion detector 34.

The optimum CID gas pressure calculation table 51b stores a predetermined CID gas pressure (or a predetermined CID gas supply pressure or supply flow rate) for each of the Q1 scan mode, the high-speed mode of the MRM measurement, the high-sensitivity mode of the MRM measurement mode, and the other measurement modes. Values of the optimum CID gas pressure and the like can be appropriately determined by the mass spectrometer manufacturer. Basically, P4 is less than P5, P6, and P7, and P5 is less than P6.

In the LC/MS/MS of the present embodiment, if the operator designates a measurement mode to be executed from the input unit 52 and inputs and sets a variety of parameters necessary for this measurement mode, the controller 50 obtains a CID gas pressure corresponding to the measurement mode to be executed at this time, based on the optimum CID gas pressure calculation table 51b stored in the processing condition parameter memory 51. For example, in the case of the precursor ion scan measurement mode, the controller 50 derives P4 as the CID gas pressure. Then, when a measurement in the precursor ion scan measurement mode is performed, the controller 50 controls the CID gas supplier 35 to adjust the supply pressure or the supply flow rate such that the CID gas pressure inside the collision cell 31 is substantially equal to P4.

Because P4 is normally less than P5, P6, and P7 as described above, in the case where the precursor ion scan measurement mode and the neutral loss scan measurement mode are executed, the CID gas pressure inside the collision cell 31 is lower than in the case where other measurement modes are executed. Hence, although the CID efficiency inside the collision cell 31 becomes lower, a decrease in ion speed inside the collision cell 31 is suppressed to be small, and product ions reach the ion detector 34 with a relatively small time delay. When the graph creator 43 creates a mass spectrum, because the ion time delay is suppressed to be relatively small as described above, a mass-to-charge-ratio deviation can be small on the created mass spectrum.

Moreover, for example, if the high-speed mode of the MRM measurement mode is designated, the controller 50 derives P5 as the CID gas pressure, based on the optimum CID gas pressure calculation table 51b stored in the processing condition parameter memory 51. When this measurement mode is executed, the controller 50 controls the CID gas supplier 35 to adjust the supply pressure or the supply flow rate such that the CID gas pressure inside the collision cell 31 is substantially equal to P5. Because P5 is normally less than P6 as described above, in the case where the high-speed mode is executed, the CID gas pressure inside the collision cell 31 is lower than in the case where the high-sensitivity mode of the same MRM measurement mode is executed. Hence, although the CID efficiency inside the collision cell 31 becomes lower, ions pass through the inside of the collision cell 31 in a relatively short time, and are introduced into the rear-stage quadrupole mass filter 33. Consequently, even if the time allotted to detect product ions originating from a given compound is short, the product ions produced from precursor ions originating from the given target compound can be detected by the ion detector 34 within the allotted time. As a result, even in the high-speed mode having lower sensitivity, the ion intensity of the target compound can be reliably obtained.

Because all the above-mentioned embodiments are given as mere examples of the present invention, even if the embodiments are appropriately changed, added, or modified within the range of the gist of the present invention, the embodiments are obviously encompassed in the scope of claims of the present application.

REFERENCE SIGNS LIST

10 . . . Liquid Chromatograph Unit
11 . . . Mobile Phase Container
12 . . . Pump
13 . . . Injector
14 . . . Column
20 . . . Mass Spectrometer
21 . . . Ionization Chamber
22, 23 . . . Intermediate Vacuum Chamber
24 . . . Analysis Chamber
25 . . . Electrospray Ionization Probe
26 . . . Heated Capillary
27 . . . Ion Guide
28 . . . Skimmer
29 . . . Ion Guide
30 . . . Front-Stage Quadrupole Mass Filter
31 . . . Collision Cell
32 . . . Multi-Pole Ion Guide
33 . . . Rear-Stage Quadrupole Mass Filter
34 . . . Ion Detector
35 . . . CID Gas Supplier
36 . . . Power Source
40 . . . Data Processor
41 . . . Data Collector
42 . . . Data Memory
43 . . . Graph Creator
44 . . . Quantitative Analyzer
50 . . . Controller
51 . . . Processing Condition Parameter Memory
51a . . . Dwell Time Calculation Table
51b . . . Optimum CID Gas Pressure Calculation Table
52 . . . Input Unit
53 . . . Display

The invention claimed is:

1. A tandem quadrupole mass spectrometer, comprising:
a front-stage quadrupole mass filter for selecting, as precursor ions, ions having a specific mass-to-charge-ratio from among a variety of ions;
a collision cell for causing the precursor ions to collide with a predetermined gas to dissociate the ions;
a rear-stage quadrupole mass filter for selecting ions having a specific mass-to-charge-ratio from among a variety of product ions produced through the dissociation;
a detector for detecting the selected product ions;
a gas supplier for supplying the predetermined gas to an inside of the collision cell; and
a controller configured to receive a measurement mode to be executed out of a plurality of selectable measurement modes, the plurality of selectable measurement modes being set by a user and comprising a first measurement mode in which the front stage quadrupole mass filter performs a mass scan and ions are dissociated inside the collision cell and a second measurement mode in which the front-stage quadrupole mass filter does not perform a mass scan;

the controller configured to control a CID gas pressure inside the collision cell in accordance with the first measurement mode when the first measurement mode is set by the user and to control the CID gas pressure inside the collision cell in accordance with the second measurement mode when the second measurement mode is set by the user;

wherein a variety of parameters necessary for each of the first measurement mode and the second measurement mode are set by the user, wherein, when the first measurement mode is set, the parameters necessary for the first measurement mode include the mass-to-charge-ratio of precursor ions to be selected by the front-stage quadrupole mass filter and the mass-to-charge-ratio of product ions to be selected by the rear-stage quadrupole mass filter;

wherein, when the second measurement mode is set, the parameters necessary for the second measurement mode include the mass-to-charge-ratio of product ions to be selected by the rear-stage quadrupole mass filter;

wherein, the first measurement mode includes a multiple reaction monitoring (MRM) measurement mode including at least the following optionally executed sub-modes: a high-speed sub-mode and a high-sensitivity sub-mode, the high-speed sub-mode having a higher measurement speed than the high-sensitivity sub-mode and the high-sensitivity sub-mode having a higher detection sensitivity than the high-speed sub-mode, and wherein, the CID gas pressure inside the collision cell is lower in a case where the measurement mode is the high-speed sub-mode of the MRM measurement mode, compared with a case where the measurement mode is the high-sensitivity sub-mode of the MRM measurement mode.

2. The tandem quadrupole mass spectrometer according to claim 1,
wherein the CID gas pressure is lower in a case where the measurement mode is the first measurement mode compared with a case where the measurement mode is the second measurement mode.

3. The tandem quadrupole mass spectrometer according to claim 2, wherein the first measurement mode includes the following optionally executed sub-modes: a precursor ion scan measurement sub-mode; a neutral loss scan measurement sub-mode; and a sub-mode in which only the front-stage quadrupole mass filter performs the mass scan while the rear-stage quadrupole mass filter does not perform ion selection according to a mass-to-charge-ratio.

4. The tandem quadrupole mass spectrometer according to claim 1, further comprising a memory, wherein a predetermined CID gas pressure for each of the respective different measurement modes is stored in the memory, and
wherein the controller is configured to control the CID gas supplier to adjust the supply pressure such that the CID gas pressure inside the collision cell is substantially equal to the stored predetermined CID gas pressure corresponding to the set measurement mode.

5. A measurement method using a tandem quadrupole mass spectrometer including a front-stage quadrupole mass filter; a collision cell; and a rear-stage quadrupole mass filter, the method comprising:
setting a measurement mode to be executed out of a plurality of measurement modes, the plurality of measurement modes comprising a first measurement mode in which the front stage quadrupole mass filter performs a mass scan and ions are dissociated inside the collision cell and a second measurement mode in which the front-stage quadrupole mass filter does not perform a mass scan;
controlling a CID gas pressure inside the collision cell in accordance with the first measurement mode when the first measurement mode is set, and controlling the CID gas pressure inside the collision cell in accordance with the second measurement mode when the second measurement mode is set;
when the first measurement mode is set, dissociating precursor ions of a target compound selected by the front-stage quadrupole mass filter in the collision cell, thereby producing product ions of the target compound; and
detecting the product ions, thereby determining a mass-to-charge-ratio of the target compound; wherein
the first measurement mode includes a multiple reaction monitoring (MRM) measurement mode including at least the following optionally executed sub-modes: a high-speed sub-mode and a high-sensitivity sub-mode, the high-speed sub-mode having a higher measurement speed than the high-sensitivity sub-mode and the high-sensitivity sub-mode having a higher detection sensitivity than the high-speed sub-mode, and
the CID gas pressure inside the collision cell is lowered in a case where the measurement mode is the high-speed sub-mode of the MRM measurement mode, compared with a case where the measurement mode is the high-sensitivity sub-mode of the MRM measurement mode.

6. The measurement method according to claim 5,
wherein the CID gas pressure is lower in a case where the measurement mode is the first measurement mode compared with a case where the measurement mode is the second measurement mode.

7. The measurement method according to claim 6, wherein the first measurement mode includes the following optionally executed sub-modes: a precursor ion scan measurement sub-mode; a neutral loss scan measurement sub-mode; and a sub-mode in which only the front-stage quadrupole mass filter performs the mass scan while the rear-stage quadrupole mass filter does not perform ion selection according to a mass-to-charge-ratio.

8. The measurement method according to claim 5,
wherein a predetermined CID gas pressure is stored for each of the different measurement modes respectively, and
wherein the controller controls the CID gas supplier to adjust the supply pressure such that the CID gas pressure inside the collision cell is substantially equal to the stored predetermined CID gas pressure corresponding to the set measurement mode.

* * * * *